US006020376A

United States Patent [19]
Pariza et al.

[11] Patent Number: 6,020,376
[45] Date of Patent: *Feb. 1, 2000

[54] METHODS OF TREATING ANIMALS TO MAINTAIN OR INCREASE CD-4 AND CD-8 CELL POPULATIONS

[75] Inventors: Michael W. Pariza; Xiaoyun Yang, both of Madison, Wis.

[73] Assignee: Wisconsin Alumni Research Foundation, Madison, Wis.

[ * ] Notice: This patent is subject to a terminal disclaimer.

[21] Appl. No.: 09/170,604

[22] Filed: Oct. 13, 1998

Related U.S. Application Data

[62] Division of application No. 08/912,614, Aug. 18, 1997, Pat. No. 5,827,885, which is a division of application No. 08/458,956, Jun. 2, 1995, Pat. No. 5,674,901, which is a continuation-in-part of application No. 08/456,988, Jun. 1, 1995, abandoned.

[51] Int. Cl.[7] ............................ A61K 31/20; A01N 63/00
[52] U.S. Cl. ....................... 514/558; 514/560; 424/93.45
[58] Field of Search ..................................... 514/558, 560; 424/93.45; 435/134, 252.9, 853

[56] References Cited

U.S. PATENT DOCUMENTS

| | | | |
|---|---|---|---|
| 4,603,142 | 7/1986 | Burger et al. | 514/456 |
| 4,868,001 | 9/1989 | Maruta | 426/623 |
| 4,888,326 | 12/1989 | Horrobin | 514/27 |
| 5,017,614 | 5/1991 | Pariza et al. | 514/558 |
| 5,070,104 | 12/1991 | Pariza et al. | 514/549 |
| 5,162,337 | 11/1992 | Elbrecht et al. | 514/300 |
| 5,208,356 | 5/1993 | Pariza et al. | 554/79 |
| 5,428,072 | 6/1995 | Cook et al. | 514/560 |
| 5,430,066 | 7/1995 | Cook et al. | 514/558 |
| 5,504,114 | 4/1996 | Cook et al. | 514/558 |
| 5,554,646 | 9/1996 | Cook et al. | 514/560 |
| 5,674,901 | 10/1997 | Cook et al. | 514/558 |
| 5,827,885 | 10/1998 | Cook et al. | 514/558 |
| 5,837,733 | 11/1998 | Pariza et al. | 514/549 |
| 5,856,149 | 1/1999 | Pariza et al. | 435/134 |

FOREIGN PATENT DOCUMENTS

| | | |
|---|---|---|
| 0 524 796 A1 | 7/1992 | European Pat. Off. . |
| 0 579 901 A1 | 3/1993 | European Pat. Off. . |
| 0 641 562 A1 | 9/1994 | European Pat. Off. . |
| WO 96/06605 | 5/1995 | WIPO . |
| WO96/38137 | 3/1996 | WIPO . |

OTHER PUBLICATIONS

Begin, M.E., et al., "Plasma Fatty Acid Levels in Patients with Acquired Immune Deficiency Syndrome and in Controls," *Prostaglandins Leukotrienes and Essential Fatty Acids*, 37:135–137 (1989).

Chin, Sou F., et al., "Conjugated Linoleic Acid (9,11– and 10,12– Octadecadienoic Acid) Is Produced in Conventional but Not Germ–Free Rats Fed Linoleic Acid," *Nutrient metabolism*, pp. 694–701 (1994).

Chin et al., "Synthesis of CLA by Intestinal Microorganisms," *FASEB J. 7*, A169 (1993).

Chin et al., "Synthesis of CLA by Intestinal Microorganisms," *Food Research Institute*, 1992 Annual Report, p. 139–140.

Cook, Mark E., "Exogenous Antigen Challenge and Its Effect on Nutrient Metabolism," Proceedings American Association of Swine Practitioners 25th Annual Meeting (1994).

Cook, et al., "Immune Modulation by Altered Nutrient Metabolism: Nutritional Control of Immune–Induced Growth Depression: Symposium: The Microenvironment of Immune Tissue," *Poultry Science*, 72:1301–1305 (1993).

Das, U.N., "Can Essential Fatty Acid Deficiency Predispose to AIDS?", *Can. Med. Assoc. J.*, 132:900–902 (Apr. 15, 1995).

Eyssen et al., "Biotransformation of Linoleic Acid and Bile Acids by *Eubacterium lentum*," *Applied and Environmental Microbiology*, 47:39–43 (1984).

Fairbank et al., "Octadeca–9–11 Dienoic Acid in Diagnosis of Cervical Intraepithelial Neoplasia," *Lancet* p. 329 (1988).

Fujimoto et al., "Biohydrogenation of Linoleic Acid by Anaerobic Bacteria Isolated from Rumen," *Biosci. Biotech. Biochem.* 57:1026–1027 (1993).

Ha, Y.L., et al., "Anticarcinogens from fried ground beef: heat–altered derivatives of linoleic acid," *Carcinogenesis*, 8(12):1881–1887 (1987).

Ha, Y.L., et al., "Newly Recognized Anticarcinogenic Fatty Acids: Identification and Quantification in Natural and Processed Cheese," *J. Agric. Food Chem.*, 37(1):75–81 (1989).

Haumann, B., "Conjugated Linoleic acid offers research promise," *Inform.* 7:152–159 (1996).

Ip et al., "Mammary Cancer Prevention by Conjugated Dienoic Derivative of Linoleic Acid," *Cancer Research*, 51,6118–6124 (1991).

Jack et al., "Serum octadeca–9, 11 dienoic–acid—an assay of free radical activity or a result of bacterial production?," *Clinica Chimica Acta*, 224:139–146 (1994).

Kemp et al., "The Hydrogenation of Unsaturated Fatty Acids by Five Bacterial Isolates from the Sheep Rumen, Including a New Species," *Journal of General Microbiology*, 90:100–114 (1975).

Kepler et al., "Biohydrogenation of Unsaturated Fatty Acids," *Journal of Biological Chemistry*, 245:3612–3620 (1970).

(List continued on next page.)

*Primary Examiner*—Kevin E. Weddington
*Attorney, Agent, or Firm*—Quarles & Brady LLP

[57] ABSTRACT

Methods of treating animals to maintain or elevate CD-4 and CD-8 cell levels and to prevent or alleviate the adverse effects on the animal caused by the production or exogenous administration of tumor necrosis factor (TNF) or by a virus consist of administering to the animal a safe and effective amount of a conjugated linoleic acid (CLA) or a substance which is converted in the animal into CLA. A method of preparing CLA employing a bacteria isolated from a rat colon also is disclosed.

5 Claims, 4 Drawing Sheets

OTHER PUBLICATIONS

Klein, A., et al., "Progress of HIV Infection And Changes in The Lipid Membrane Structure of CD4+Cells," *AIDS*, 6(3):332–333 (1992).

Kohn, A., et al., "Unsaturated Free Fatty Acids Inactivate Animal Enveloped Viruses," *Archives of Virology*, 66:301–307 (1980).

Kumar, G. Sravan, et al., "Effect of n–6 and n–3 Fatty Acids on the Proliferation of Human Lymphocytes and Their Secretion of TNF–a and IL–2 in Vitro," *Nutrition Research*, 12:815–823 (1992).

Lee et al., "Conjugated Linoleic acid and atherosclerosis in rabbits," *Atherosclerosis*, 108:19–25 (1994).

The Merck Index, Tenth Edition (1983), p. 790.

Michel, et al., "Interaction of Conjugated Dienoic Derivatives of Linoleic Acid with β–Carotene on Cellular Host Defense," *Fed. Am. Soc. Exp. Biol. J.*, 6:A1102 (1992).

Miller, et al., "Feeding Conjugated Linoleic Acid to Animals Partially Overcomes Catabolic Response Due to Endotoxin Injection," *Biochemical and Biophysical Research Communications*, 198(3):1107–1112 (1994).

Mills et al., "Hygrogenation of $C_{18}$ Unsaturated Fatty Acids by Pure Cultures of A Rumen Micrococcus," *Aust. J. Biol. Sci.*, 23:1109–1113 (1970).

Nicolosi et al., "Dietary Conjugated Linoleic Acid Reduces Aortic Fatty Streak Formation Greater Than Linoleic Acid in Hypercholesterolemic Hamsters," *Circulation*, 88(suppl):24–58 (1993).

Pariza, M.W., Food Research Institute 1988 Annual Fall Meeting, (Oct. 12, 1988).

Peck, Michael D., et al., "The Esterified Plasma Fatty Acid Profile Is Altered in Early HIV–1 infection," *Lipids*, 28(7):593–597(1993).

Thompson et al., "Measurement of The Diene Conjugated Form of Linoleic Acid in Plasma by High Performance Liquid Chromatography: A Questionable Non–Invasive Assay of Free Radical Activity?," *Chem. Biol. Interactions*, 55:357–366 (1985).

Uchida, K., "Occurrence of Conjugated Dienoic Fatty Acids in The Cellular Lipids of *Pediococcus homari*," *Agr. Biol. Chem.*, 39(2):561–563 (1975).

Verhulst et al., "Isomerization of Polyunsaturated long Chain Fatty Acids of Propionibacteria," *System. Appl. Microbiol.*, 9:12–15 (1987).

Verhulst et al., "Biohydrogenation of Linoleic Acid by *Clostridium sporogenes*, *Clostridium bifermentans*, *Clostridium sordellii* and Baceriodes sp.," *FEMS Microbiology Ecology*, 31:255–259 (1985).

METHODS OF TREATING ANIMALS TO MAINTAIN OR INCREASE CD-4 AND CD-8 CELL POPULATIONS

STATEMENT OF RELATED CASES

This is a division of application Ser. No. 08/912,614, filed Aug. 18, 1997, now U.S. Pat. No. 5,827,885 which was a division of application Ser. No. 08/458,956, filed Jun. 2, 1995, now U.S. Pat. No. 5,674,901, which was a continuation-in-part of application Ser. No. 08/456,988, filed Jun. 1, 1995, abandoned.

FIELD OF THE INVENTION

The present application generally relates to methods of treating animals, including humans. More particularly, it relates to methods of treating animals by maintaining or increasing the CD-4 and CD-8 lymphocyte cell populations or levels in said animals. It is known that maintaining or increasing CD-4 and CD-8 cell populations in an animal can benefit its immune system.

BACKGROUND OF THE INVENTION

Researchers have observed anorexia and weight loss or reduction in weight gain in humans and animals that have been exposed to immune stimulants, such as endotoxin (LPS). The intraperitoneal injection of lipopolysaccharide (i.e. endotoxin) into chickens decreases food intake and growth rate for 24 hours, alters nutrient metabolism, and induces fever.

Recent studies (Klasing et al., 1987, J Nutr. 117:1629) have confirmed that the vaccination of domestic fowl with several immune stimulants also can result in a substantial reduction in feed intake and induce weight loss or decrease in weight gain. In a study recently conducted with white Pekin ducks, two vaccinations reduced final carcass weight by as much as 0.4 lbs./bird and breast meat by 0.075 lbs./bird. Broilers and Single Comb White Leghorns (egg laying chickens) also have been observed to have reduced weight gains following immune stimulation. The potential losses due to immune stimulation costs the poultry industry millions of dollars per year. At the present time, antibiotics are used to prevent such weight loss, but the use of antibiotics for this purpose is expensive and not without disadvantages.

In a similar manner anorexia, weight loss, and reduced growth of humans that are subjected to chronic immune stimulation because of infections, surgery, or exposure to immune stimulants is devastating to health and well being.

The mechanism by which immune stimulation causes anorexia, weight loss and reduced growth is known to be mediated by products, such as catabolic hormones, released following immune stimulation (e.g., the macrophage cytokine known as interleukin-1 or IL-1). The production of IL-1 from macrophages simultaneously stimulates T-cells to release IL-2, an anticarcinogenic compound which is desirable, but the release of IL-1 and other catabolic hormones from stimulated macrophages and possibly other immune-regulated cells induces an undesirable systemic reduction in skeletal muscle synthesis and increased muscle degradation resulting in weight loss or a decline in weight gain. Thus, while IL-1 and related immune hormones are essential cytokines for immune function, their systemic hormonal effects are devastating and have prevented its acceptance for immune therapy.

It is known that other biological products produced by immune cells, such as tumor necrosis factor (TNF) also can cause adverse physiological changes in animals, including anorexia and cachexia, and it has been observed that viral infections of animals can have similar adverse effects on the animals. It also has been observed that viral infections, especially HIV infections, can undesirably deplete the CD-4 (helper T cells) and CD-8 (cytotoxic T cells) cell populations in infected animals, including humans.

It would be advantageous to have methods of maintaining or elevating CD-4 and CD-8 cell populations in animals to bolster or benefit their immune systems and methods for preventing or alleviating the adverse effects of the production or exogenous administration of TNF and viral infections in animals.

BRIEF SUMMARY OF THE INVENTION

It is one object of the present invention to disclose a method of maintaining or elevating CD-4 and CD-8 cell levels in animals to bolster or benefit their immune systems.

It also is an object of the present invention to disclose a method for preventing or alleviating the adverse effects caused by the production or exogenous administration of TNF in animals, including humans.

It is another object to disclose a method of preventing or alleviating the adverse effects caused by viral infections in animals, including humans.

It also is an object to disclose novel methods of producing conjugated linoleic acids (CLA) for use in such methods.

We have discovered that a method comprising the administration to an animal of safe and effective amounts of the conjugated linoleic acids 9,11-octadecadienoic acid and 10,12-octadecadienoic acid (CLA) or a substance that is converted in the animal to CLA can maintain and elevate the CD-4 and CD-8 cell levels and bolster or benefit the immune systems of those animals.

We also have discovered that methods comprising the administration of the CLA prevent or alleviate the weight loss and other adverse effects that can result from the production and exogenous administration of TNF in animals, including humans, or from the infection of the animals, including humans, by viruses. It is possible that the beneficial effects of CLA in preventing or alleviating the adverse effects of TNF and virus are due to its ability to maintain or elevate CD-4 and CD-8 cell levels.

We also have discovered a method of producing CLA which comprises using a strain of Lactobacillus which converts free linoleic acid into CLA.

It will be apparent to those skilled in the art that the forementioned objects and other advantages may be achieved by the practice of the present invention.

DESCRIPTION OF THE PREFERRED EMBODIMENT

In the preferred method of the present invention for maintaining or increasing CD-4 and CD-8 cells, a safe and effective amount of conjugated linoleic acid (CLA) or a substance that is converted to CLA in the animal is administered to an animal, including a human, to maintain or elevate the CD-4 and/or CD-8 cell levels in the animal.

In the preferred method of the present invention for preventing or alleviating the effects of TNF, a safe and effective amount of conjugated linoleic acid (CLA) or a substance that is converted to CLA in the animal is administered to an animal, including a human, which is likely to or is producing catabolic inducing levels of tumor necrosis factor (TNF) or which is likely to or is receiving catabolic inducing levels of exogenously administered TNF, to prevent weight loss and other adverse effects which can result from the systemic effects of TNF. Because of the differences in size and susceptibility of animals, including humans, to the adverse effects of systemically released or exogenously applied TNF, the amounts which are safe and effective will vary considerably.

In the preferred method of the present invention for preventing or alleviating the adverse effects of viruses, a safe amount of CLA or a substance which is converted in the animal to CLA is administered to an animal, including a human, which is likely to be infected by a virus or vaccinated with a virus, or which has a viral infection. The amount which is administered, in addition, to being safe also is an amount which is effective to prevent or counteract the adverse effects of anorexia and other catabolic effects caused by the viral infection or vaccination.

Since CLA is a natural food ingredient and it is relatively non-toxic, the amounts which can be administered in the methods of the invention are not critical as long as they are enough to be effective.

In the preferred method for making CLA a biologically pure culture of Lactobacillus (ATCC No. 55739) is incubated in a medium containing essential nutrients and free linoleic acid under ambient conditions to produce CLA.

The practice of the present invention is further illustrated by the examples which follow:

EXAMPLE 1

In two experiments, day old broiler chicks were fed a diet containing either 0 or 0.5% CLA. The chicks were fed the dietary treatments for approximately 4 weeks then placed on the control diet. Within two weeks following the CLA feeding period, blood samples were collected and mononuclear cells were isolated by density gradient centrifugation. The cells were then treated with FITC conjugated monoclonal antibodies that were specific for CD-4 (helper T cell lymphocytes) and CD-8 (cytotoxic T cell lymphocyte). Using flow cytometry, and propidium iodide to separate dead cells from live cells, the percentage of CD-4 and CD-8 cells in the isolated mononuclear cell isolation were enumerated.

Figure 1:
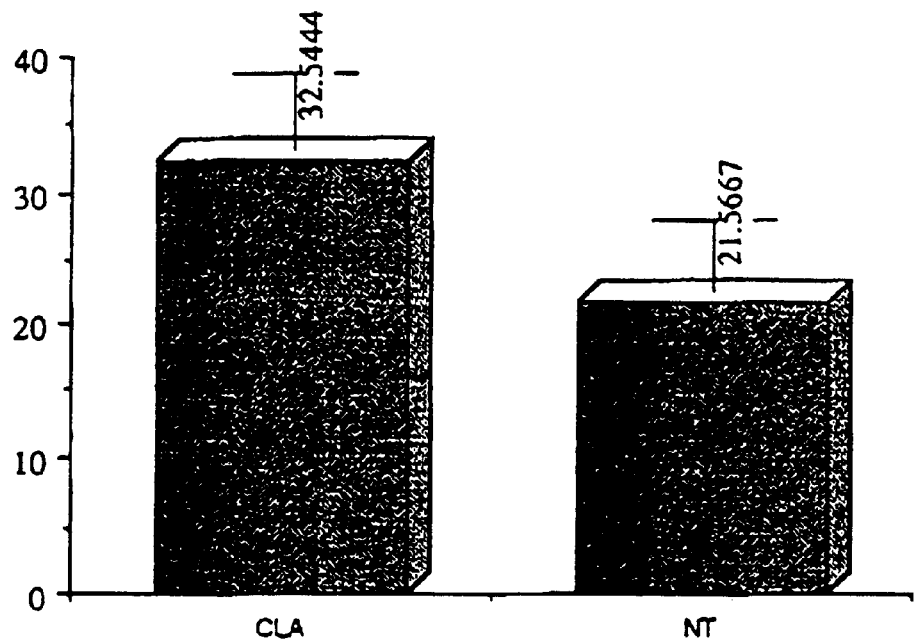
FIG. 1 is a graph showing the percent increase in the number of CD-4 positive cells in chicks given CLA as compared to control chicks (NT)
Figure 2:
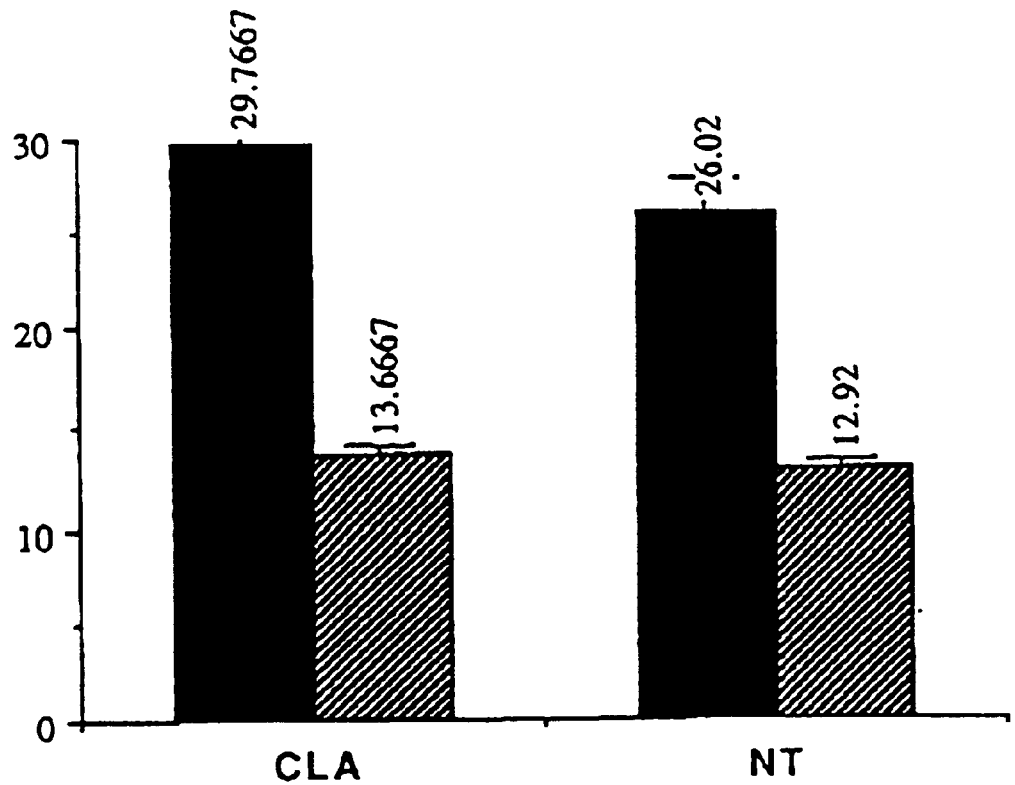
FIG. 2 is a graph showing the percent increase in CD-4 positive cells (solid) and CD-8 positive cells (striped) in chicks given CLA and control chicks (NT)
Figure 3:
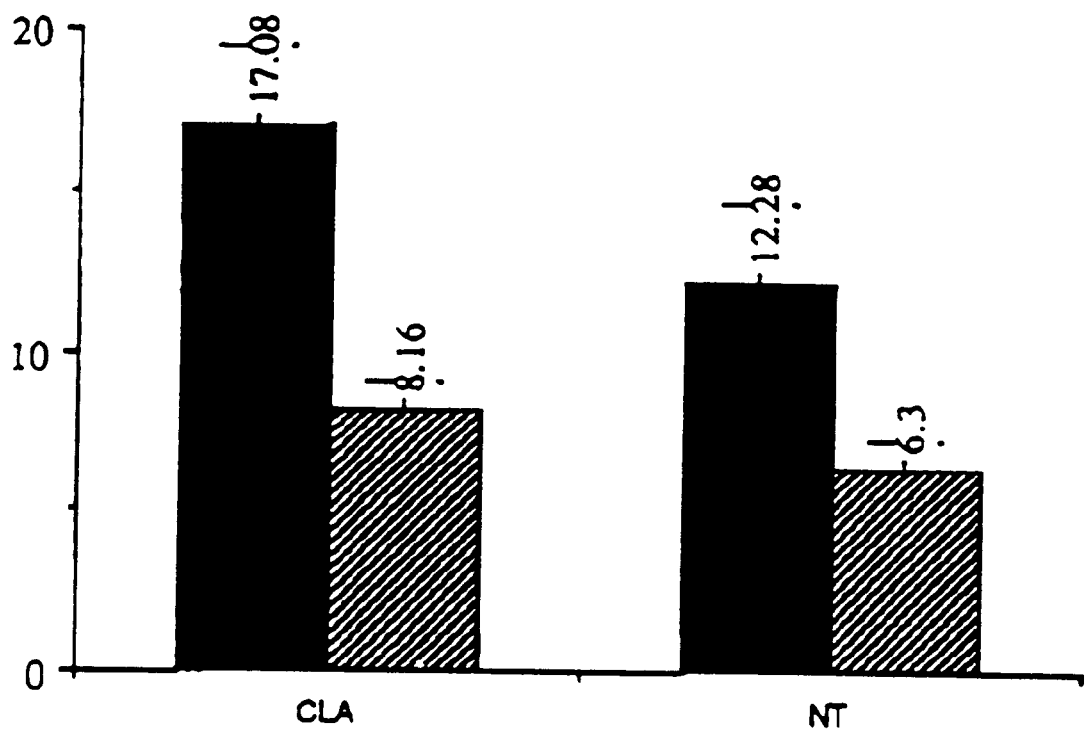
FIG. 3 is a graph like FIG. 2 showing the results of a second experiment.

In experiment 1, only CD-4 cells were counted. CLA feeding markedly enhanced the percent of CD-4 cells in the mononuclear cell fraction as seen in FIG. 1. In experiment 2, replicate analyses were conducted at two time points, three days apart on March 30 (FIG. 2) and again Apr. 2, 1995 (FIG. 3). In experiment 2, both CD-4 and CD-8 cells were enumerated. In both analyses, CLA enhanced the percent of CD-4 and CD-8 cells in the mononuclear fraction. In addition, the CD-4/CD-8 ratios were increased 7 and 8% in the March and April analyses, respectively.

EXAMPLE 2

Four pens of 10 chicks were fed a standard poultry ration with 0.5% lard (controls) or with 0.5% CLA mixed daily (2 pens per treatment). When the chicks were 3 weeks of age, they were weighed, inoculated with 100 µg of $E.$ $coli$ 0111:B4 endotoxin i.p. to stimulate the immune system. Chicks were again weighed 24 h later. While the chicks fed the unsupplemented diet failed to gain body weight following endotoxin exposure, the chicks fed CLA gained 10 grams (p<0.07) (Table I). Antibody responses to sheep red blood cells demonstrated that CLA had no effect on antibody synthesis.

TABLE I

| Treatment | Av. Initial Wt. | Av. Wt. 24 h post endotoxin | Av. initial 24 h | % with no or negative gain |
|---|---|---|---|---|
| Control | 311 ± 12 | 311 ± 12 | 0 ± 3 | 53 |
| .5% CLA | 305 ± 9 | 315 ± 9 | 10 ± 4 | 27 |

EXAMPLE 3

Another group of chicks was fed a diet containing 0.5% CLA which was mixed with the feed daily. At 3 weeks of age the chicks were inoculated i.p. with 750 µg $E.$ $coli$ 055:B5 endotoxin to stimulate immunity or phosphate buffered saline (PBS) as a control. The control chicks injected with PBS gained 9 g over the following 24 h period, and the CLA fed, PBS injected chicks gained 13.5 g. When chicks fed the control diet were injected with endotoxin, they lost 1.3 g of body weight over the following 24 h period. However, the CLA fed chicks even after endotoxin injection continued to gain an average of 6.6 g.

The results of the examples demonstrate that a lower proportion of chicks lose weight, within 24 hours of being injected with endotoxin, when the chicks ingest an animal feed which contains CLA. In fact, the results show that not only do a fewer number of birds lose weight but that those birds that are fed CLA actually gain considerably more weight than the control birds. In addition, the loss of body weight in rats following stimulation was 50% of those not fed CLA.

In addition to using CLA as an animal feed additive (e.g. poultry feed) to enhance growth and prevent weight loss by diminishing the effects of immune stimulation, CLA is useful as an immune modulator (e.g. IL-1 inhibitor). The adverse or harmful catabolic effects of systemic IL-1 may be alleviated by adding CLA to the food of animals, including humans, experiencing weight loss associated with acute or chronic diseases.

EXAMPLE 4

A group of seven rats was fed a semi-purified diet to which CLA was not added; a second group was fed the same diet containing 0.5% CLA. Three weeks later the animals were weighed. Four animals from each group were inoculated with endotoxin (1 mg/kg body weight); the remaining three animals from each group were inoculated with PBS. Rats fed the control diet and injected with PBS gained 7.4 g. Rats fed the CLA-containing diet and injected with PBS gained 5.4 g. Rats fed control diet and injected with endotoxin lost 21.05 g. Rats fed CLA-containing diet and injected with endotoxin lost only 11.9 g.

In another embodiment of the invention, a substance, such as a fatty acid, that is converted into CLA or which modulates the level of CLA in the body of an animal is fed. Specifically, we have found that free linoleic acid is converted to CLA in the bodies of rats, probably by microorganisms in the gastrointestinal system (S. F. Chin, W. Liu, K. Albright, and M. W. Pariza, 1992, FASEB J. 6:Abstract #2665).

EXAMPLE 5

A group of seven rats was fed a semi-purified diet containing 5% corn oil; a second group was fed the same diet with corn oil but also containing added free linoleic acid (0.5%). Three weeks later the animals were weighed. Four animals from each group were inoculated with endotoxin (1 mg/kg body weight); the remaining three animals from each group were inoculated with PBS. Rats fed the control diet and injected with PBS gained 7.4 g. Rats fed the diet to which linoleic acid had been added, and injected with PBS, gained 7.2 g. Rats fed control diet and injected with endotoxin lost 21.05 g. Rats fed diet to which linoleic acid had been added, and injected with endotoxin, lost only 11.4 g. We believe these results are due to the conversion of added linoleic acid to CLA within the body of rats as discussed above.

EXAMPLE 6

Mice were fed either a control diet (n=16) or 0.5% conjugated linoleic acid (CLA). After 28 days on the dietary treatments, mice within each treatment were divided into 2 groups of 8 mice. One group, within each dietary treatment, was injected with phosphate buffer saline (PBS, control injection) and the other group was injected with tumor necrosis factor (TNF at 200 ug/kg body weight). Change in body weight for 72 hours following TNF injection relative to its PBS injected control was determined.

Figure 4:
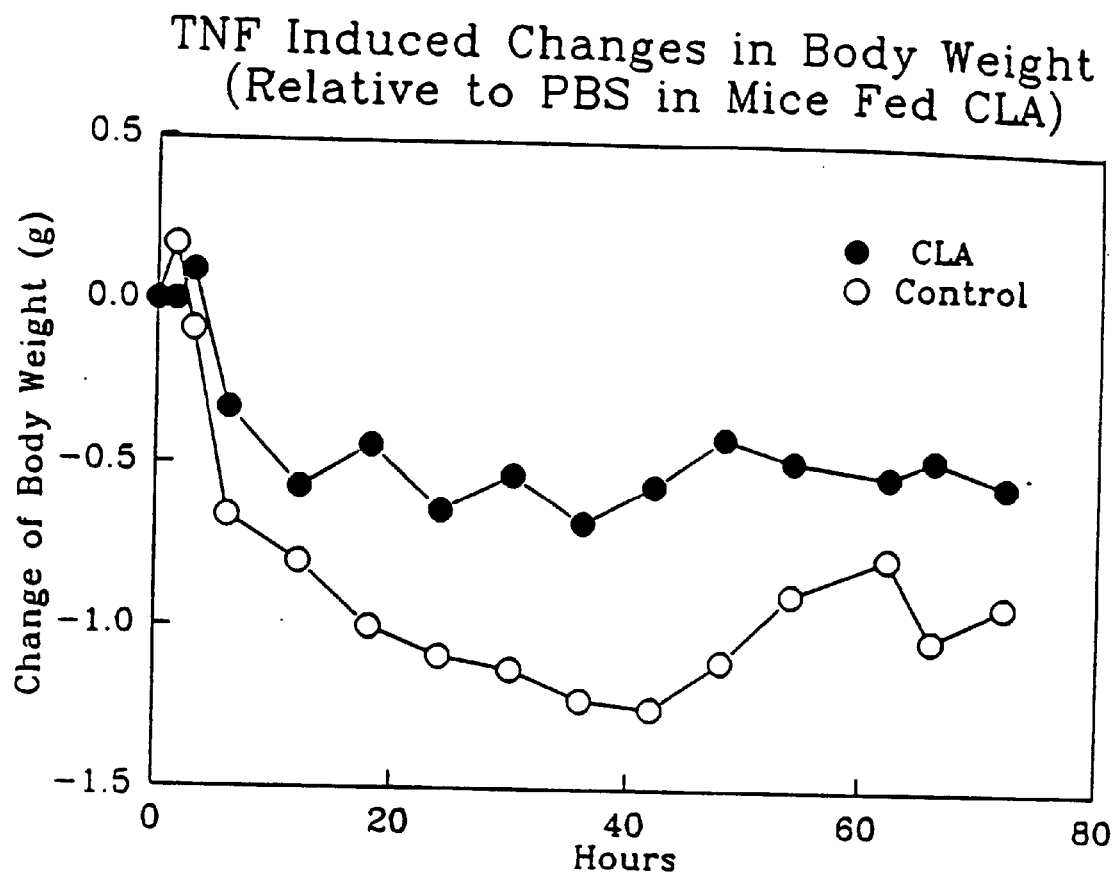
FIG. 4 is a graph showing the differences in the TNF induced effects on body weight in control mice and on mice fed CLA.

FIG. 4 shows that the CLA fed mice lost less weight (relative to their PBS injected controls) than the TNF injected control fed mice.

EXAMPLE 7

Four pens of 8 to 9 day old chicks were fed 0 or 0.5% CLA for 3 weeks. After the 3 week feeding period, one pen of chicks per dietary treatment received a wing web injection of live attenuated fowl pox virus. The other pen for each dietary treatment served as the nonchallenged control. Growth, feed intake, and feed conversion for the 24 hour period following the virus inoculation was determined. Changes relative to the nonchallenged control were determined.

Table II shows that chicks fed the control diet and injected with fowl pox virus gained only 69% as much as those fed the control diet but not challenged with virus. These viral challenged chicks however consumed 90% more feed and had 30% poorer feed conversion than their nonchallenged counterparts. In contrast, the chicks fed CLA and injected with fowl pox virus performed very similar to their CLA fed nonchallenged controls.

TABLE II

Effects of fowl pox (live attenuated virus) injections on the 24-hr growth, feed intake, and feed conversion of 4-week-old leghorn chicks fed control or CLA (.5%) diets.

| Dietary treatment | % of noninjected control* | | |
|---|---|---|---|
| | 24-hr gain | 24-hr intake | 24-hr feed conversion |
| Control | 69 | 190 | 130 |
| CLA | 94 | 106 | 100 |

*Treatment groups responding close to 100% are responding similarly to noninjected controls.

EXAMPLE 8

Isolation and Characterization of Conjugated Linoleic Acid (CLA)-Producing Bacteria Conventional rats, after being fed 5% linoleic acid for 4 to 8 weeks, have a significantly higher CLA concentration in their tissue than germ-free rats on the same diet. Based on this observation, we attempted to isolate CLA-producing bacterial strains from the intestinal tracts of conventional rats.

Samples of bacteria from the colons of conventional rats were cultured on conventional MRS, BHI and PDA agar plates. 15 colonies isolated from aerobic incubation and 30 colonies from anaerobic incubation at 37° C. were picked for further evaluation. The 45 cultures in total were screened for conversion of linoleic acid to CLA with HPLC and GC. Only 4 of the strains isolated from MRS under anaerobic conditions had the ability to produce CLA from the linoleic acid. Among them, one strain was selected because it produced the highest CLA as measured by HPLC. The CLA produced by the strain was the cis-9, trans-11 form of conjugated linoleic acid. The selected strain produced the highest amount of CLA after a 36-hour incubation at 37° C.

The preferred microorganism is a Gram positive, catalase-negative, bacteria which forms non-motile rods. It grows at 45° C. but not at 15° C., and is considered to be *Lactobacillus fermentum* or *L. reuteri*. A biologically pure culture of the bacteria has been deposited with the American Type Culture Collection, Rockville, Md., U.S.A. as ATCC No. 55739. Detailed biochemical characteristics of the organism are set forth in Table III.

TABLE III

Biochemical characteristics of CLA-producing isolate belonging to the genus Lactobacillus

| | | | |
|---|---|---|---|
| Indole production | – | Cellobiosidase | – |
| N-Actylglucosaminidase | – | Esculin pH | – |
| α-Glucocidase | – | Esculin hydralysis | – |
| α-Arabinosidase | – | Glycogen | – |
| β-Glucosidase | – | Lactosidase | weak |
| α-Fucosidase | – | Maltosidase | weak |
| Phosphatase | – | Mannitolase | – |
| α-Galactosidase | + | Melezitosidase | – |
| β-Galactosidase | + | Raffinosidase | weak |
| Indoxyl-acetate | + | Rhamnosidase | weak |
| Arginine utilization | + | Salicinase | – |
| Leucine aminopeptidase | + | Xylosidase | – |
| proline aminopeptidase | – | Nitrate utilization | + |
| Pyroglutamic acid arylamidase | – | Hemolysis | – |
| Tyrosine aminopeptidase | – | Bile green utilization | – |
| Arginine aminopeptidase | + | | |

TABLE III-continued

Biochemical characteristics of CLA-producing
isolate belonging to the genus Lactobacillus

| | |
|---|---|
| Alanine aminopeptidase | + |
| Histidine aminopeptidase | + |
| Phenylalanine aminopeptidase | + |
| Glycine aminopeptidase | − |
| Catalase | − |

The methods of the present invention may take several embodiments. In one embodiment, the CLA is added to an animal's feed or to a human's food. In another embodiment, the CLA can be administered to an animal in a pharmaceutical or veterinary composition containing a safe and effective dose of the CLA. In a third embodiment, the animal can be fed a safe amount of the substances which will form the CLA in situ in the animal or human.

The animal feeds and pharmaceutical preparations for use in the methods of the present invention are those containing the free conjugated linoleic acids (CLA) 9,11-octadecadienoic acid and 10,12-octadecadienoic acid in combination with a conventional animal feed (e.g. poultry feed), human food supplement, or approved pharmaceutical diluent. Active forms of CLA also include compositions containing the active isomers of CLA; non-toxic salts thereof; active esters and other active chemical derivatives thereof; and mixtures thereof. Animals and humans may also be given a substance such as linoleic acid which is converted to CLA within the body, or which may modulate intracellular levels of CLA or otherwise mimic the beneficial effects of CLA in mitigating anorexia, weight loss, and other adverse effects from the abnormal production of TNF or a viral infection.

The free conjugated linoleic acids (CLA) have been previously isolated from fried meats and described as anticarcinogens by Y. L. Ha, N. K. Grimm and M. W. Pariza, in Carcinogenesis Vol. 8, No. 12, pp. 1881–1887 (1987). Since then, they have been found in some processed cheese products (Y. L. Ha, N. K. Grimm and M. W. Pariza, in J. Agric. Food Chem., Vol. 37, No. 1, pp. 75–81 (1987)). However, animal feeds containing CLA, or its non-toxic derivatives, such as the sodium and potassium salts, as an additive in combination with conventional animal feeds or human foods are novel.

The free acid forms of the CLA may be prepared by isomerizing linoleic acid. The non-toxic salts of the free CLA acids may be made by reacting the free acids with a non-toxic base. Natural CLA may also be prepared from linoleic acid by the action of $W^{12}$-Cis, $W^{11}$-transisomerase from a harmless microorganism such as the Rumen bacterium *Butyrivibrio fibrisolvens*. Harmless microorganisms in the intestinal tracts of rats and other monogastric animals may also convert linoleic acid to CLA (S. F. Chin, W. Liu, K. Albright and M. W. Pariza, 1992, FASEB J.6:Abstract #2665).

The CLA may also be prepared by use of the bacteria of Example 8 which will synthesize CLA from linoleic acid. The resulting CLA is both stable and easily extracted from the fermentation broth.

Another convenient way of supplying CLA is by use of a milk product naturally enriched with CLA. The milk can be prepared by adding a source of free linoleic acid and the harmless bacteria of Example 8 to milk and incubating the mixture for about 1 hour at 37° C. or until the linoleic acid is converted into CLA.

The CLA obtained by the practice of the described methods of preparation contains one or more of the 9,11-octadecadienoic acids and/or 10,12-octadecadienoic acids and active isomers thereof. It may be free or bound chemically through ester linkages. The CLA is heat stable and can be used as is, or dried and powdered. The CLA is readily converted into a non-toxic salt, such as the sodium or potassium salt, by reacting chemically equivalent amounts of the free acid with an alkali hydroxide at a pH of about 8 to 9.

Theoretically, 8 possible geometric isomers of 9,11- and 10,12-octadecadienoic acid (c9,c11; c9,t11; t9,c11; t9,t11; c10,c12; c10,t12; t10,c12 and t10,t12) would form from the isomerization of c9,c12-octadecadienoic acid. As a result of the isomerization, only four isomers (c9,c11; c9,t11; t10, c12; and c10,c12) would be expected. However, of the four isomers, c9,t11- and t10,c12-isomers are predominantly produced during the autoxidation or alkali-isomerization of c9,c12-linoleic acid due to the co-planar characteristics of 5 carbon atoms around a conjugated double-bond and spatial conflict of the resonance radical. The remaining two c,c-isomers are minor contributors.

The relatively higher distribution of the t,t-isomers of 9,11- or 10,12-octadecadienoic acid apparently results from the further stabilization of c9,t11- or t10,c12-geometric isomers, which is thermodynamically preferred, during an extended processing time or long aging period. Additionally the t,t-isomer of 9,11- or 10,12-octadecadienoic acid that was predominantly formed during the isomerization of linoleic acid geometrical isomers (t9,t12-, c9,t12- and t9,c12-octadecadienoic acid) may influence the final ratio of the isomers or the final CLA content in the samples.

Linoleic acid geometrical isomers also influence the distribution of minor contributors (c,c-isomers of 9,11- and 10,12-, t9,c11- and c11,t12-octadecadienoic acids). The 11,13-isomer might be produced as a minor product from c9,c12-octadecadienoic acid or from its isomeric forms during processing.

The CLA and its non-toxic derivatives, such as the non-toxic salts, in addition to being added to an animal's feed or human food or formed in situ can be administered in the form of pharmaceutical or veterinary compositions, such as tablets, capsules, solutions or emulsions to the animal or the humans. The exact amount to be administered, of course, depends upon the form of CLA employed, the route of administration, and the nature of the animal's or human's condition. Generally, the amount employed of CLA and its non-toxic salts employed as a pharmaceutical will range from about one part per million (ppm) to about 10,000 ppm of CLA in the animal's or human's diet. However, the upper limit of the amount to be employed is not critical because CLA is relatively non-toxic and it is a normal constituent of the human diet (including human breast milk). The amounts to be added to a conventional animal feed or human's food as an additive can range from 0.01% to 2.0% or more by weight of the animal's or human's food.

The preferred pharmaceutical and veterinary compositions of CLA contain the non-toxic sodium or potassium salt of CLA in combination with a pharmaceutical diluent. When the compositions are solutions or suspensions intended for oral administration the diluent will be one or more diluents, such as lactose or starch, and the product will be a tablet, capsule or liquid. When the compositions are solutions or suspensions intended for parenteral administration the preferred diluent will be Sterile Water for Injection U.S.P.

The mechanism by which viral infections cause the adverse effects of anorexia and weight loss in animals may be due to the depletion of CD-4 and/or CD-8 cell levels and the stimulation of immune cells to release catabolic hormones, such as TNF. However, it is possible that viral infections increase the exposure to bacterial endotoxins caused by secondary bacterial infections. In addition, to the fowl pox virus of Example 7, the method of the present invention can be useful in treating animals, including humans, which are exposed to viruses or which have viral infections in which the virus family is any virus, including one of the following: Picornavirus, Togavirus, Paramyxovirus, Orthomyxovirus, Rhabdovirus, Reovirus, Retrovirus, Bunyavirus, Coronavirus, Arenavirus, Parvoviruses, Papovavirus, Adenovirus, Herpevirus, Poxvirus.

Undesirable catabolic amounts of TNF occur in patients which have cancer, infectious diseases, vaccinations and exposure to immune stimulants. The catabolic effects of TNF may be due to the depletion of CD-4 and CD-8 cells due to a lack of CLA in human and animal diets.

It will be readily apparent to those skilled in the art that a number of modifications or changes may be made without departing from the spirit and scope of the present invention. Therefore, the invention is only to be limited by the claims.

We claim:

1. A method of preparing a conjugated linoleic acid (CLA) which comprises incubating a Lactobacillus strain that converts linoleic acid to a CLA, in a nutrient medium that comprises free linoleic acid for a time sufficient to convert linoleic acid to CLA.

2. A conjugated linoleic acid enriched milk product made by the process of claim 1 in which the medium is milk based.

3. The method of claim 1 wherein the Lactobacillus is incubated under aerobic conditions.

4. The method of claim 1, wherein the Lactobacillus is incubated under anaerobic conditions.

5. The method of claim 1, wherein the Lactobacillus is ATCC 55739.

* * * * *